US008173168B2

(12) United States Patent
Platz et al.

(10) Patent No.: US 8,173,168 B2

(45) Date of Patent: *May 8, 2012

(54) DISPERSIBLE MACROMOLECULE COMPOSITIONS AND METHODS FOR THEIR PREPARATION AND USE

(75) Inventors: Robert M. Platz, Half Moon Bay, CA (US); Thomas K. Brewer, Walnut Creek, CA (US); Terence D. Boardman, Palo Alto, CA (US)

(73) Assignee: Novartis Pharma AG, Basel (CH)

( * ) Notice: Subject to any disclaimer, the term of this patent is extended or adjusted under 35 U.S.C. 154(b) by 713 days.

This patent is subject to a terminal disclaimer.

(21) Appl. No.: 11/536,348

(22) Filed: Sep. 28, 2006

(65) Prior Publication Data

US 2007/0020199 A1 Jan. 25, 2007

Related U.S. Application Data

(63) Continuation of application No. 10/403,482, filed on Mar. 31, 2003, now Pat. No. 7,138,141, which is a continuation of application No. 10/007,868, filed on Nov. 9, 2001, now Pat. No. 6,592,904, which is a continuation of application No. 09/498,397, filed on Feb. 4, 2000, now Pat. No. 6,423,344, which is a continuation of application No. 08/644,681, filed on May 8, 1996, now Pat. No. 6,051,256, which is a continuation-in-part of application No. 08/423,515, filed on Apr. 14, 1995, now Pat. No. 6,582,728, which is a continuation-in-part of application No. 08/383,475, filed on Feb. 1, 1995, now abandoned, which is a continuation-in-part of application No. 08/207,472, filed on Mar. 7, 1994, now abandoned.

(51) Int. Cl.

*A61K 9/14* (2006.01)

*A61K 9/16* (2006.01)

(52) U.S. Cl. ........................................ 424/489; 424/499

(58) Field of Classification Search .................. 424/489, 424/491, 497, 499, 514, 2, 3, 5, 12

See application file for complete search history.

(56) References Cited

U.S. PATENT DOCUMENTS

| | | | |
|---|---|---|---|
| 2,598,525 | A | 4/1950 | Fox |
| 3,362,405 | A | 1/1968 | Hazel |
| 3,425,600 | A | 2/1969 | Abplanalp |
| 3,674,901 | A | 7/1972 | Shepherd et al. |
| 3,770,207 | A | 11/1973 | Muller et al. |
| 3,790,079 | A | 2/1974 | Berglund et al. |

(Continued)

FOREIGN PATENT DOCUMENTS

EP 0 072046 2/1983

(Continued)

OTHER PUBLICATIONS

Moses, A. C., Diabetes, vol. 32, Nov. 1983, pp. 1040-1047.*

(Continued)

*Primary Examiner* — Gollamudi Kishore

(74) *Attorney, Agent, or Firm* — Lisa Matovcik

(57) ABSTRACT

A process for preparing ultrafine powders of biological macromolecules comprises atomizing liquid solutions of the macromolecules, drying the droplets formed in the atomization step, and collecting the particles which result from drying. By properly controlling each of the atomization, drying, and collection steps, ultrafine dry powder compositions having characteristics particularly suitable for pulmonary delivery for therapeutic and other purposes may be prepared.

106 Claims, 4 Drawing Sheets

U.S. PATENT DOCUMENTS 3,825,188 A 7/1974 Doering
3,921,637 A 11/1975 Bennie et al.
3,964,483 A 6/1976 Mathes
3,991,304 A 11/1976 Hillsman
3,991,761 A 11/1976 Cocozza
3,994,421 A 11/1976 Hansen
4,035,317 A 7/1977 Gershberg
4,036,223 A 7/1977 Obert
4,052,255 A 10/1977 Hackbarth et al.
4,069,819 A 1/1978 Valentini et al.
4,098,273 A 7/1978 Glenn
4,127,235 A 11/1978 Klaile et al.
4,153,689 A 5/1979 Hirai et al.
4,211,769 A 7/1980 Okada et al.
4,221,339 A 9/1980 Yoshikawa
4,249,526 A 2/1981 Dean et al.
4,253,468 A 3/1981 Lehmbeck
4,261,793 A 4/1981 Nakamura et al.
4,268,460 A * 5/1981 Boiarski et al. .................. 261/1
4,294,624 A 10/1981 Veltman
4,294,829 A 10/1981 Suzuki et al.
4,305,210 A 12/1981 Christensen et al.
4,338,931 A 7/1982 Cavazza
4,446,862 A 5/1984 Baum et al.
4,452,239 A 6/1984 Malem
4,476,804 A 10/1984 Glatt et al.
4,484,577 A 11/1984 Sackner et al.
4,486,435 A 12/1984 Schmidt et al.
4,503,035 A 3/1985 Pestka et al.
4,534,343 A 8/1985 Nowacki et al.
4,540,602 A 9/1985 Motoyama et al.
4,590,206 A 5/1986 Forrester et al.
4,613,500 A * 9/1986 Suzuki et al. ................ 424/85.4
4,624,251 A 11/1986 Miller
4,627,432 A 12/1986 Newell et al.
4,649,911 A 3/1987 Knight et al.
4,659,696 A 4/1987 Hirai et al.
4,677,975 A 7/1987 Edgar et al.
4,698,328 A 10/1987 Neer et al.
4,702,799 A 10/1987 Tuot
4,721,709 A 1/1988 Seth et al.
4,739,754 A 4/1988 Shaner
4,748,034 A 5/1988 de Rham
4,760,093 A 7/1988 Blank et al.
4,784,878 A 11/1988 Haak
4,790,305 A 12/1988 Zoltan et al.
4,794,167 A 12/1988 Lindner et al.
4,807,814 A 2/1989 Douche et al.
4,811,731 A 3/1989 Newell et al.
4,818,424 A 4/1989 Evans et al.
4,819,629 A 4/1989 Jonson
4,823,784 A 4/1989 Bordoni et al.
4,833,125 A 5/1989 Neer et al.
4,835,187 A 5/1989 Reuter et al.
4,866,051 A 9/1989 Hunt et al.
4,871,489 A 10/1989 Ketcham
4,884,565 A 12/1989 Cocozza
4,889,114 A 12/1989 Kladders
4,907,583 A 3/1990 Wetterlin et al.
4,926,852 A 5/1990 Zoltan et al.
4,942,544 A 7/1990 McIntosh et al.
4,946,828 A 8/1990 Markussen
4,952,402 A 8/1990 Sparks et al.
4,968,607 A 11/1990 Dower et al.
4,984,158 A 1/1991 Hillsman
4,995,385 A 2/1991 Valentini et al.
5,000,888 A 3/1991 Kilbride, Jr. et al.
5,009,367 A 4/1991 Nielsen
5,011,678 A 4/1991 Wang et al.
5,017,372 A 5/1991 Hastings
5,026,550 A 6/1991 Aeschbach et al.
5,027,806 A 7/1991 Zoltan et al.
5,033,463 A 7/1991 Cocozza
5,035,237 A 7/1991 Newell et al.
5,038,769 A 8/1991 Krauser
5,042,975 A 8/1991 Chien et al.
5,048,514 A 9/1991 Ramella
5,049,388 A 9/1991 Knight et al.
5,066,522 A 11/1991 Cole et al.
5,081,228 A 1/1992 Dower et al.
5,093,316 A 3/1992 Lezdey et al.
5,098,893 A 3/1992 Franks et al.
5,099,833 A 3/1992 Michaels
5,113,855 A 5/1992 Newhouse
5,139,016 A 8/1992 Waser
5,161,524 A 11/1992 Evans
5,180,812 A 1/1993 Dower et al.
5,186,164 A 2/1993 Raghuprasad
5,200,399 A 4/1993 Wettlaufer et al.
5,204,108 A 4/1993 Illum
5,206,219 A * 4/1993 Desai ................................ 514/3
5,206,306 A 4/1993 Shen
5,221,731 A 6/1993 Weymans et al.
5,230,884 A 7/1993 Evans et al.
5,232,707 A 8/1993 Lokensgard
5,235,969 A * 8/1993 Bellm ...................... 128/200.18
5,254,330 A * 10/1993 Ganderton et al. ............. 424/46
5,260,306 A 11/1993 Boardman et al.
5,269,980 A 12/1993 Levendis et al.
5,279,708 A 1/1994 Wood et al.
5,290,765 A 3/1994 Wettlaufer et al.
5,295,479 A 3/1994 Lankinen
5,302,581 A 4/1994 Sarin et al.
5,309,900 A 5/1994 Knoch et al.
5,320,094 A 6/1994 Laube et al.
5,320,714 A 6/1994 Brendel
5,331,953 A 7/1994 Andersson et al.
5,354,562 A 10/1994 Platz et al.
5,354,934 A 10/1994 Pitt et al.
5,364,838 A 11/1994 Rubsamen
5,376,359 A 12/1994 Johnson
5,376,386 A 12/1994 Ganderton et al.
5,384,133 A 1/1995 Boyes et al.
5,458,135 A 10/1995 Patton et al.
5,482,927 A 1/1996 Maniar et al.
5,487,378 A * 1/1996 Robertson et al. ....... 128/200.16
5,506,203 A 4/1996 Backstrom et al.
5,518,709 A 5/1996 Sutton et al.
5,518,998 A 5/1996 Backstrom et al.
5,580,856 A 12/1996 Prestrelski et al.
5,607,697 A 3/1997 Alkire et al.
5,622,657 A 4/1997 Takada et al.
5,624,530 A 4/1997 Sadykhov et al.
5,628,937 A 5/1997 Oliver et al.
5,648,096 A 7/1997 Gander et al.
5,651,990 A 7/1997 Takada et al.
5,667,806 A 9/1997 Kantor
5,687,905 A 11/1997 Tsai
5,707,644 A * 1/1998 Illum ............................ 424/434
5,723,269 A 3/1998 Akagi et al.
5,741,478 A 4/1998 Osborne et al.
5,776,491 A 7/1998 Allen, Jr. et al.
5,800,598 A 9/1998 Chein et al.
5,807,576 A 9/1998 Allen, Jr. et al.
5,855,913 A 1/1999 Hanes et al.
5,874,064 A 2/1999 Edwards et al.
5,922,253 A 7/1999 Herbert et al.
5,924,216 A 7/1999 Takahashi
5,964,416 A 10/1999 Jaeger et al.
5,970,974 A 10/1999 Van Der Linden et al.
5,976,574 A 11/1999 Gordon
5,985,248 A 11/1999 Gordon et al.
5,985,309 A 11/1999 Edwards et al.
5,993,805 A 11/1999 Sutton et al.
5,997,848 A 12/1999 Patton et al.
6,001,336 A 12/1999 Gordon
6,015,546 A 1/2000 Sutton et al.
6,017,310 A 1/2000 Johnson et al.
6,022,525 A 2/2000 Sutton et al.
6,051,256 A 4/2000 Platz et al.
6,051,257 A * 4/2000 Kodas et al. .................. 424/489
6,077,543 A 6/2000 Gordon et al.
6,117,455 A 9/2000 Takada et al.
6,123,924 A 9/2000 Mistry et al.
6,149,941 A 11/2000 Schwarz et al.
6,153,129 A 11/2000 Herbert et al.
6,156,511 A 12/2000 Schatz et al.

| | | | |
|---|---|---|---|
| 6,308,434 | B1 | 10/2001 | Chickering, III et al. |
| 6,331,290 | B1 | 12/2001 | Morgan |
| 6,331,310 | B1 | 12/2001 | Roser et al. |
| 6,365,190 | B1 | 4/2002 | Gordon et al. |
| 6,383,810 | B2 | 5/2002 | Fike et al. |
| 6,416,739 | B1 | 7/2002 | Rogerson et al. |
| 6,423,344 | B1 | 7/2002 | Platz et al. |
| 6,455,028 | B1 | 9/2002 | Wulffhart et al. |
| 6,503,480 | B1 | 1/2003 | Edwards et al. |
| 6,565,885 | B1 | 5/2003 | Tarara et al. |
| 6,572,893 | B2 | 6/2003 | Gordon et al. |
| 6,582,728 | B1 | 6/2003 | Platz et al. |
| 6,592,904 | B2 | 7/2003 | Platz et al. |
| 6,656,492 | B2 | 12/2003 | Kajiyama et al. |
| 2002/0081266 | A1 | 6/2002 | Woolfe et al. |
| 2002/0175225 | A1 | 11/2002 | Boersen et al. |
| 2003/0124193 | A1 | 7/2003 | Snyder et al. |
| 2003/0203036 | A1 | 10/2003 | Gordon et al. |
| 2003/0215514 | A1 | 11/2003 | Platz et al. |

FOREIGN PATENT DOCUMENTS

| | | |
|---|---|---|
| EP | 0 122036 | 10/1984 |
| EP | 0 237507 | 9/1987 |
| EP | 0 344375 | 12/1989 |
| EP | 0 347779 | 12/1989 |
| EP | 0 360340 | 3/1990 |
| EP | 0 383569 | 8/1990 |
| EP | 0 408801 | 1/1991 |
| EP | 0 461930 | 12/1991 |
| EP | 0 467172 | 1/1992 |
| EP | 0 468914 | 1/1992 |
| EP | 4 69725 | 2/1992 |
| EP | 0 490797 | 6/1992 |
| EP | 0 506293 | 9/1992 |
| EP | 5 12693 | 11/1992 |
| EP | 0 611567 | 8/1994 |
| EP | 6 28331 | 12/1994 |
| EP | 0 677332 | 10/1995 |
| EP | 6 74541 | 10/1995 |
| EP | 6 81843 | 11/1995 |
| EP | 7 09085 | 5/1996 |
| EP | 9 72526 | 1/2000 |
| EP | 1 004349 | 5/2000 |
| FR | 2 257351 | 8/1975 |
| GB | 473471 | 10/1937 |
| GB | 621785 | 4/1949 |
| GB | 1 527605 | 8/1975 |
| GB | 2 105189 | 3/1983 |
| NL | 7 712041 | 5/1979 |
| SU | 0 628930 | 10/1978 |
| SU | 1 003926 | 1/1979 |
| WO | WO 88/04556 | 6/1988 |
| WO | WO 88/07870 | 10/1988 |
| WO | WO 88/09163 | 12/1988 |
| WO | WO 90/07351 | 7/1990 |
| WO | WO 90/09780 | 9/1990 |
| WO | WO 90/11139 | 10/1990 |
| WO | WO 90/15635 | 12/1990 |
| WO | WO 91/02545 | 3/1991 |
| WO | WO 91/02558 | 3/1991 |
| WO | WO 91/16882 | 11/1991 |
| WO | WO 92/18164 | 10/1992 |
| WO | WO 93/02712 | 2/1993 |
| WO | WO 93/07465 | 4/1993 |
| WO | WO 93/09832 | 5/1993 |
| WO | WO 94/08552 | 4/1994 |
| WO | WO 94/08627 | 4/1994 |
| WO | WO 95/00127 | 1/1995 |
| WO | WO 95/00128 | 1/1995 |
| WO | WO 95/13864 | 5/1995 |
| WO | WO 95/23613 | 9/1995 |
| WO | WO 95/24183 | 9/1995 |
| WO | WO 95/31479 | 11/1995 |
| WO | WO 96/03978 | 2/1996 |
| WO | WO 96/05809 | 2/1996 |
| WO | WO 96/09814 | 4/1996 |
| WO | WO 96/11580 | 4/1996 |
| WO | WO 96/15814 | 5/1996 |
| WO | WO 96/32096 | 10/1996 |
| WO | WO 96/32149 | 10/1996 |
| WO | WO 97/03649 | 2/1997 |
| WO | WO 97/28788 | 8/1997 |
| WO | WO 97/36574 | 10/1997 |
| WO | WO 97/36578 | 10/1997 |
| WO | WO 97/41833 | 11/1997 |
| WO | WO 97/44067 | 11/1997 |
| WO | WO 98/01228 | 1/1998 |
| WO | WO 98/29096 | 7/1998 |
| WO | WO 98/29098 | 7/1998 |
| WO | WO 98/31346 | 7/1998 |
| WO | WO 98/47493 | 10/1998 |
| WO | WO 99/16419 | 4/1999 |
| WO | WO 99/16422 | 4/1999 |
| WO | WO 99/17742 | 4/1999 |
| WO | WO 99/30834 | 6/1999 |
| WO | WO 99/31019 | 6/1999 |
| WO | WO 99/32083 | 7/1999 |
| WO | WO 99/64014 | 12/1999 |
| WO | WO 00/00176 | 1/2000 |
| WO | WO 00/09084 | 2/2000 |
| WO | WO 00/10541 | 3/2000 |
| WO | WO 00/12278 | 3/2000 |
| WO | WO 00/13668 | 3/2000 |
| WO | WO 00/66256 | 11/2000 |
| WO | WO 00/76673 | 12/2000 |
| WO | WO 01/03673 | 1/2001 |
| WO | WO 01/13885 | 3/2001 |
| WO | WO 01/15664 | 3/2001 |
| WO | WO 01/45731 | 6/2001 |
| WO | WO 01/64188 | 9/2001 |
| WO | WO 01/87278 | 11/2001 |
| WO | WO 02/09669 | 2/2002 |
| WO | WO 02/15880 | 2/2002 |
| WO | WO 02/078675 | 10/2002 |
| WO | WO 03/000202 | 1/2003 |

OTHER PUBLICATIONS

Barj et al. "Submicronic MgAI204 Powder Synthesis in Supercritical Ethanol." J. of Materials Sci. vol. 27. No. 8 p. 2187-2192 (1992).

Bjork, E. et al., "Degradable Starch Microspheres As a Nasal Delivery System for Insulin." International Journal of Pharmaceutics. 1988. vol. 47. pp. 233-238.

Bloch et al., "Dispersions of Hydrochlorothiazide and Chlorhalidone in Pentaerythritol." Pharm. Acta. Helv. (1983) , 58 (1):, p. 14-22.

Bohnet. Matthias, "Calculation and Design of Gas/Solid-Injectors," Powder Tech, 1984. pp. 302-313.

Budrik, G. K. et al.. "Ejector Feeders for Pneumat:ic Transport Systems," Chemical Petroleum Engineering. Sep.-Oct. 1978. vol. 14, Nos. 9-10. pp. 9-10.

Byron, P. R. et al. "Drug Delivery Via the Respiratory Tract," Journal or Aerosol Medicine, 1994. vol. 7, No. 1. pp. 49-75.

Carpenter, John F. et al., "Modes of Stabilization of a Protein by Organic Solutes During Desiccation," Cryobiology. 1988. vol. 25, pp. 459-470.

Chien, Y. W. et al.. "Intranasal Drug Delivery for Systemic Medications," Critical Reviews in Therapeutic Drug Carries Systems. 1987, vol. 4, Issue 2, pp. 67-92. (1 Page).

Colthorpe P. et al., "The pharmacokinetics of pulmonary-delivered insulin: a comparison of intratracheal and aerosol administration to the rabbit.," Pharmaceutical Research. 1992. vol. 9. No. 6, pp. 764-768. (1 page).

Duchateau. G. et al . "Bile Salts and Intranasal Drug Absorption," International Journal of Pharmaceutics, 1986. vol. 31. pp. 193-199.

Elliott, et: al . "Parenteral Absorption of Insulin From the Lung in Diabetic Children." .Aust:. Paediatr. J. 1987, vol. 23. pp. 293-297.

EP Search Report dated Dec. 16, 2005 for Application No. 97926420.7.

Fox, et al., "Performance of a Venturi Eductor as a Feeder in a Pneumatic Conveying System." Powder & Bulk Engineering. Mar. 1988. pp. 33-36.

Friedman. T., "Progress Toward Human Gene Therapy," Science, Jun. 16, 1989, vol. 244, pp. 1275-1281.

Gansslen, M., "Uber Inhalation Von Insulin," Klin. Wochenschr, Jan. 1925, vol. 4, p. 71. with translation included (3 pages).

Govinda Rao, A. R., "Aerosol Insulin Inhalation Enquiry," Indian J. Physiol. Pharmacol, 1959. vol. 3, pp. 161-167.
Habener. Joel F., "Parathyroid Hormone: Secretion and Metabolism In Vivo," Proc. Nat. Acad. Sci. USA. Dec. 1971. vol. 68. No. 12, pp. 2986-2991.
Hastings, et al., "Clearance of Different-Sized Proteins from the Alveolar Space in Humans and Rabbits," J.Appl. Physiol., 1192, vol. 73, pp. 1310-1316. (1 page).
He et al., "Chitosan Microspheres Prepared by Spray Drying," International J. of Pharm. (Amsterdam), vol. 187, No. 1, pp. 53-65.
Hesch, R. D., "Pulsatile secretion of parathyroid hormone and its action on a type I and type II PTH receptor: a hypothesis for understanding osteoporosis," Calcified Tissue Int. 1988, vol. 42. pp. 341-344.
Hino et al., "Development of a new type nozzle and spray-drier for industrial production of fine powders", European J. of Pharmaceutics and Biopharmaceutics (2000), vol. 49, pp. 79-85.
Hubbard, Richard C. and Ronald G. Cryscal, "Abstract Strategies for aerosol therapy of alpha 1-antitrypsin deficiency by the aerosol route.." Lung. 1990, vol. 168, Supplement: 1990, Proceedings of the 8th Congress of SEP. Edited by H. Matthys, pp. 565-578.
Kohler, Dieter ec al., "Nicht Radioaktives Verfahren Zur Messung' Der Lung'enpermeabilitat: Inhalation Von Insulin," Atemu. Lunaenkrkh. Jahraana. 19B7, vol. 13. No. 5, pp. 230-232. For English Abstract see Schluter Reference.
Laube. Beth L. et al., "Preliminary study of the efficacy of insulin aerosol delivered by oral inhalation in diabetic patients." JAMA. Apr. 28, 1993, vol. 269. No. 16. pp. 2106-2109. (1 page).
Lee, Shih-Wei et al., "Development of an aerosol dosage form containing insulin," Journal of Pharmaceutical Sciences. vol. 65, No. 4, Apr. 1976, pp. 567-572. (1 page).
Liu, Fang-Yu et al., "Pulmonary Delivery of Free and Liposomal Insulin," Pharmaceutical Research 1993, vol. 10. No. 2. pp. 228-232.
Masters, "The Process Stages of Spray Drying: Atomization", Spray Drying Handbook, pp. 230-247.
Nagai, Tsuneji et al., "Powder Dosage Form of Insulin for Nasal Administration," Journal of Controlled Release. 1984. vol. 1, pp. 15-22.
Neer, 2. M. et al.."The Use of Parathyroid Hormone Plus 1,25-Dihydroxyvitamin D to Increase Trabecular Bone in Osteoporotic Men and Poscmenopausal Women," Osteoporosis. 1987, vol. 53. pp. 829-835.
Nieminen, M. M. et al., "Aerosol Deposition in Automatic Dosimeter NebUlization." Eur. J. Resir. Dis. 1987, vol. 71. PC. 145-152. (1 page).
Partial EP Search Report dated Jan. 4, 2006 for Application No. 97926420.7.
Patton, John S. et al., "(D) Routes of Delivery: Case Studies—(2) Pulmonary Delivery of Peptides and Proteins for Systemic Action," Advanced Drug Delivery Reviews. 1992. vol. 8, pp. 179-196.
Pikal, Michael et al., "Moisture Transfer From Stopper to Product and Resulting Stability Implications," Develooments in Bioloaical Standardardization. 1991., vol. 74, International Symposium on Biological Product Freeze-Drying and Formulation, pp. 1.
Pikal, Michael J., "Polymorphisms in Pharmaceutical Solids," AAPS. Nov. 5, 1992. Annual Meeting and Expositions, San Antonio, TX. 2 pages.
Pittman, et al., "Pneumatic Conveying of Bulk Solids Using a Vacuum Aerated Feed Nozzle." Solid Handling Conference Paper C4. Jun. 10-12, 1986 Thames Polytechnic London, United Kingdom, pp. C41-CS1.
Rosenfeld, et al., "Adenovirus-Mediated Transfer of a Recombinant a-1-Antitrypsin Gene to the Lung Epithelium in Vivo," Science. vol. 252, Apr. 19, 1991. pp. 431-434.
Ryden, Lena et al., "Effect of -Polymers and Microspheres on the Nasal Absorption of Insulin in Rats," International Journal of Pharmaceutics. 1992, vol. 83, pp. 1-10.
Sakr, Farouk M., "A New Approach for Insulin Delivery Via The Pulmonary Route: Design and Pharmacokinetics in Non-Diabetic Rabbits," International Journal of Pharmaceutics. 1992, vol. 86, pp. 1-7. (1 page).
Schluter, Klaus J. et al., "Pulmonary Administration of Human Insulin in Volunteers and Type I-Diabetics," Abstract Reproduction Form for Annual Meeting Program Published in Diabetes. Feb. 1, 1.984. one page.
Stribling et: al., "The Mouse As a Model for Cationic Liposome-Based, Aerosolized Gene Delivery," Journal of Biooharmaceutical Sciences. 1992, 3(1./2), pp. 255-263.
Underwood, et al., "A Novel Technique for the Administration of Bronchodilator Drugs Formulated As Dry Powders to the Anaesthetized Guinea Pig," Journal of Pharmacological Methods. 1991. vol. 26. pp. 203-210.
Wigley, Frederick et al., "Insulin Across Respiratory Mucosae by Aerosol Delivery," Diabetes. 1971, vol. 20, No. 8, pp. 552-556. (1 page).
Witham, Clyde L., "Dry Dispersion With Sonic Velocity Nozzles," Workshop on Dissemination Techniques for Smoke and Obscurants Chemical Systems Laboratory. Aberdeen Proving Group, MD, Mar. 14-16, 1983, pp. 1-26.
Yoshida, H., "Absortion of Insulin Delivered to Rabbit Trachea Using Aerosol Dosage Form," Journal of Pharmaceutical Sciences. May 1979, vol. 68, No. 5, pp. 670-671. (1 page).
Zholob, V. M. et al., "Effect of Injector Unit Design on the Particle Size of Atomized Powder," 0038-5735/79/1806, 1.97.9 Plenum Publishing Corporation, pp. 362-364, Dnepropetrovsk State University, Translated from Poroshkovava Metalluraiva.
Mumenthaler et al., "Feasibility Study on Spray-Drying Protein Pharmaceuticals: Recombinant Human Growth Hormaoine and Tissue-Type Plasminogen Activator." Pharm Res. (1994), 11(1):. p. 12-20.
EPO Communication dated Nov. 2, 2006 for European Application No. 97926420.7.
Examiner's Report for Slovak Republic Patent Application No. PP 0146-2006-2001.
de Boer, et al. "Air classifier technology (ACT) in dry powder inhalation Part 2. The effect of lactose carrier surface properties on the drug-to-carrier interaction in adhesive mixtures for inhalation," International Journal of Pharmaceutics, vol. 260, 2003 Elsevier Science B.V., pp. 201-216.
European Examination Report dated Jun. 11, 2008 for European Application No. 97 926 420.7-1216.
Ferrari, et al. "The Surface Roughness of Lactose Particles Can Be Modulated by Wet-Smoothing Using a High-Shear Mixer," AAPS PharmSciTech, Dec. 2004; vol. 5, No. 4, Article 60, (http://www.aapspharmscitech.org), pp. 1-6.

* cited by examiner

DISPERSIBLE MACROMOLECULE COMPOSITIONS AND METHODS FOR THEIR PREPARATION AND USE

CROSS-REFERENCE TO RELATED APPLICATIONS

The present application is a continuation of U.S. Ser. No. 10/403,482, filed Mar. 31, 2003, issued as U.S. Pat. No. 7,138,141, which is a continuation of U.S. Ser. No. 10/007,868, filed Nov. 9, 2001, issued as U.S. Pat. No. 6,592,904, which is a continuation of U.S. Ser. No. 09/498,397, filed Feb. 4, 2000, issued as U.S. Pat. No. 6,423,344, which is a continuation of U.S. Ser. No. 08/644,681, filed May 8, 1996, issued as U.S. Pat. No. 6,051,256, which is a continuation-in-part of U.S. Ser. No. 08/423,515, filed Apr. 14, 1995, issued U.S. Pat. No. 6,582,728, which is a continuation-in part of U.S. Ser. No. 08/383,475, filed Feb. 1, 1995, now abandoned, which is a continuation-in part of U.S. Ser. No. 08/207,472, filed Mar. 7, 1994, now abandoned. The full disclosures of each of these applications are herein incorporated by reference in their entirety.

BACKGROUND OF THE INVENTION

1. Field of the Invention

The present invention relates generally to macromolecule compositions and methods for their preparation and use. In particular, the present invention relates to a method for preparing macromolecule compositions by spray drying under controlled conditions which preserve protein purity and results in good powder dispersibility and other desirable characteristics.

Over the years, certain drugs have been sold in compositions suitable for forming a drug dispersion for oral inhalation (pulmonary delivery) to treat various conditions in humans. Such pulmonary drug delivery compositions are designed to be delivered by inhalation by the patient of a drug dispersion so that the active drug within the dispersion can reach the lung. It has been found that certain drugs delivered to the lung are readily absorbed through the alveolar region directly into blood circulation. Pulmonary delivery is particularly promising for the delivery of macromolecules (proteins, polypeptides, high molecular weight polysaccharides, and nucleic acids) which are difficult to deliver by other routes of administration. Such pulmonary delivery can be effective both for systemic delivery and for localized delivery to treat diseases of the lungs.

Pulmonary drug delivery can itself be achieved by different approaches, including liquid nebulizers, aerosol-based metered dose inhalers (MDI's), and dry powder dispersion devices. Aerosol-based MDI's are losing favor because they rely on the use of chlorofluorocarbons (CFC's), which are being banned because of their adverse effect on the ozone layer. Dry powder dispersion devices, which do not rely on CFC aerosol technology, are promising for delivering drugs that may be readily formulated as dry powders. Many otherwise labile macromolecules may be stably stored as lyophilized or spray-dried powders by themselves or in combination with suitable powder carriers.

The ability to deliver pharmaceutical compositions as dry powders, however, is problematic in certain respects. The dosage of many pharmaceutical compositions is often critical, so it is desirable that dry powder delivery systems be able to accurately, precisely, and reliably deliver the intended amount of drug. Moreover, many pharmaceutical compositions are quite expensive. Thus, the ability to efficiently formulate, process, package, and deliver the dry powders with a minimal loss of drug is critical. While the permeability of natural macromolecules in the lung is well known, the combined inefficiencies of macromolecule production processes and macromolecule delivery has limited commercialization of dry macromolecule powders for pulmonary delivery.

A particularly promising approach for the pulmonary delivery of dry powder drugs utilizes a hand-held device with a hand pump for providing a source of pressurized gas. The pressurized gas is abruptly released through a powder dispersion device, such as a venturi nozzle, and the dispersed powder made available for patient inhalation. While advantageous in many respects, such hand-held devices are problematic in a number of other respects. The particles being delivered are usually less than 5 μm in size, making powder handling and dispersion more difficult than with larger particles. The problems are exacerbated by the relatively small volumes of pressurized gas, which are available using hand-actuated pumps. In particular, venturi dispersion devices are unsuitable for difficult-to-disperse powders when only small volumes of pressurized gas are available with the handpump. Another requirement for hand-held and other powder delivery devices is efficiency. High device efficiency in delivering the drug to the patient with the optimal size distribution for pulmonary delivery is essential for a commercially viable product. Conventional techniques used to deliver medication do not have the delivery efficiency required for commercialization. The ability to achieve both adequate dispersion and small dispersed volumes is a significant technical challenge that requires that each unit dosage of the powdered composition be readily and reliably dispersible.

Spray drying is a conventional chemical processing unit operation used to produce dry particulate solids from a variety of liquid and slurry starting materials. The use of spray drying for the formulation of dry powder pharmaceuticals is known, but has usually been limited to small molecule and other stable drugs which are less sensitive to thermal degradation and other rigorous treatment conditions. The use of spray drying for the preparation of biological macromolecule compositions, including proteins, polypeptides, high molecular weight polysaccharides, and nucleic acids, can be problematic since such macromolecules are often labile and subject to degradation when exposed to high temperatures and other aspects of the spray drying process. Excessive degradation of the macromolecules can lead to drug formulations lacking in the requisite purity. It can also be difficult to control particle size and particle size distribution in compositions produced by spray drying. For pulmonary delivery, it is critical that the average particle size be maintained below 5 μm, preferably in the range from 0.4 μm to 5 μm, and that the amount of the composition comprising particles outside of the target size range be minimized. Preferably, at least 90% by weight of the powder will have a particle size in the range from 0.1 μm to 7 μm. More preferably, at least 95% will have a size in the range from 0.4 μm to 5μm. Moreover, it can sometimes be difficult to achieve a desired low moisture content required for physical and chemical stability in the final particulate product, particularly in an economic manner. Finally, and perhaps most important, it has been difficult to produce the small particles necessary for pulmonary delivery in an efficient manner. For high value macromolecular drugs, collection efficiencies (i.e., the amount of particulate drug recovered from the process in a useable form) should be above 80% by weight, preferably above 90% by weight, and desirably above 95% by weight. While spray drying has been used to prepare powder of macromolecules in laboratory scale equipment as described below, commercial spray driers are not designed to produce powders in the pulmonary size range. The methods for atomization, drying powder, and collection must be modified to economically produce a protein powder with the desired product characteristics for pulmonary delivery and in sufficient yield and at commercially acceptable production rates (in excess of 30 g/hr).

It is therefore desirable to provide improved methods for the spray drying of macromolecules for use in pulmonary and other drug delivery. In particular, it is desirable to provide improved process methods and powder composition which address at least some of the deficiencies listed above.

2. Description of the Related Art

U.S. Pat. Nos. 5,260,306, 4,590,206, GB 2 105 189, and EP 072 046 describe a method for spray drying nedocromil sodium to form small particles preferably in the range from 2 to 15 μm for pulmonary delivery. U.S. Pat. No. 5,376,386, describes the preparation of particulate polysaccharide carriers for pulmonary drug delivery, where the carriers comprise particles sized from 5 to 1000 μm and having a rugosity less than 1.75. Mumenthaler et al. (1994) *Pharm. Res.* 11:12 describes recombinant human growth hormone and recombinant tissue-type plasminogen activator. That study demonstrated that the proteins may degrade during spray drying and hence may not retain sufficient activity for therapeutic use. WO 95/23613 describes preparing an inhalation powder of DNase by spray drying using laboratory-scale equipment. WO 91/16882 describes a method for spray drying proteins and other drugs in liposome carriers.

The following applications assigned to the assignee of the present application each describe that spray drying may be used to prepare dry powders of biological macromolecules: application Ser. No. 08/423,515, filed on Apr. 14, 1995, now U.S. Pat. No. 6,582,728; application Ser. No. 08/383,475, now abandoned, which was a continuation-in-part of application Ser. No. 08/207,472, filed on Mar. 7, 1994, now abandoned; application Ser. No. 08/472,563, filed on Apr. 14, 1995, now abandoned, which was a continuation-in-part of application Ser. No. 08/417,507, filed on Apr. 4, 1995, now abandoned, which was a continuation of application Ser. No. 08/044,358, filed on Apr. 7, 1993, now abandoned; application Ser. No. 08/232,849, filed on Apr. 25, 1994, now U.S. Pat. No. 5,607,915, which was a continuation of application Ser. No. 07/953,397, now abandoned. WO 94/07514 claims priority from Ser. No. 07/953,397. WO 95/24183 claims priority from Ser. Nos. 08/207,472 and 08/383,475.

SUMMARY OF THE INVENTION

According to the present invention, methods for spray drying biological macromolecules provide pharmaceutical compositions having improved characteristics which overcome at least some of the deficiencies noted above with respect to prior spray drying processes. The methods of the present, invention comprise providing a predetermined concentration of the macromolecule and optionally other excipients as a solution, slurry, suspension, or the like, in a liquid medium, usually in water as an aqueous solution. The macromolecule is optionally formulated in solution with compatible excipients such as sugars, buffers, salts, and other proteins, as needed to provide a therapeutically effective dose, inhibit degradation during drying, promote powder dispersibility, and achieve acceptable physical and chemical stability of the powder at room temperature. The liquid medium is atomized under conditions selected to form droplets having an average particle size at or below a predetermined value, and the droplets are then dried under conditions selected to form particles of the formulation having a moisture content below a predetermined threshold level. The dried particles are collected and packaged in a form suitable for use, typically in a unit dosage receptacle. The conditions of atomizing and drying will preferably be selected so that the particles may be dried below the target moisture content in a single drying step, and so that the particles are produced in the desired size range without having to further separate (e.g., size classify) the particles prior to packaging.

In a first preferred aspect of the method of the present invention, the total solids content in the liquid medium (including the macromolecule and excipient(s)) will be below 10% usually being in the range between 0.5% and 10% wt. Preferably, the concentration will be in the range from about 1% wt to 5% wt, and the liquid medium will comprise an aqueous solution. It has been found that control of the concentration of the total solids below 5% significantly enhances the ability to obtain dried particles in the desired size range, i.e., below 5 μm, and preferably in the range from 0.4 μm to 5 μm.

In a second preferred aspect of the method of the present invention, the solution is atomized to produce droplets having a median droplet size at or below 11 μm. Optimization of the atomizer design and operating conditions allows the solids content to be increased to the levels described above making high volume production practical and economical. Preferably, the atomization step is performed by flowing the solution and an atomization gas stream through a two-fluid nozzle at a predetermined gas:liquid mass flow ratio, preferably above 5. The air pressure upstream of the air orifice is maintained above 25 psig. While such air pressure is above that which results in sonic velocity, i.e., the velocity does not continue to increase above sonic velocity, it has been found that increased density of the higher pressure atomization gas decreases the droplet size produced.

In another aspect of the method of the present invention, the atomized droplets are dried to form particles having a final moisture content below 5% by weight. Preferably, the particles are dried to this level in a single drying operation, typically within a single spray drying operation where the droplets are flowed concurrently with a heated gas stream having sufficient heat energy to evaporate water in the particles to the desired level before the particles are collected from the drying operation. Usually, the heated gas stream, typically a heated air stream, will have an inlet temperature of at least 90° C., preferably being at least 120° C., more preferably being at least 135° C., and still more preferably being at least 145° C., and often being 175° C., or as high as 200° C. depending on the macromolecule being dried. At least in part, the inlet temperature of the heated gas drying stream will depend on the lability of the biological macromolecule being treated. In the exemplary case of insulin, an inlet temperature in the range from 140° C. to 150° C. is preferred.

In order to control the final moisture content of the particles produced in the drying operation, it is desirable to also control the gas outlet temperature. The gas outlet temperature will be a function of the inlet temperature, the heat load imposed by the product drying step, (which depends on the inlet temperature of the liquid medium, the quantity of water to be evaporated, and the like), and other factors. Preferably, the gas outlet temperature will be maintained at at least 50° C. or above, preferably at at least 70° C., usually being in the range from 60° C. to 80° C.

In yet another specific aspect of the method of the present invention, the drying conditions will be selected to control the particle morphology in order to enhance powder dispersibility. In particular, the drying conditions are selected to provide particles having a rugosity of at least 2. Rugosity is a measure of surface convolution, with a higher number indicating a higher degree of surface irregularity. Without intending to limit the scope of the present invention in any way, it is presently believed that the increase in surface irregularity as measured by rugosity results in a decrease in cohesiveness between adjacent particles. Such decrease in surface interactions, in turn, improves the dispersibility of the resulting powders. Particle rugosity is influenced by both the drying rate of the individual droplets and the composition of the dissolved solids.

Droplets are initially dried at a relatively high rate which will create a viscous layer of material about the exterior of the liquid droplet. As the drying continues, the viscous layer is unable to flow as rapidly as the shrinking of the particle as the solvent evaporates, resulting in surface convolutions (wrinkling) of the particles. The viscosity of the viscous layer has been related to the glass transition temperature of the material by the WLF equation (Williams, Landel, Ferry Equation) ref. K. Alexander & C. J. King, Drying Technology, Vol. 3, No. 3, 1985. The temperature gradient within the drying zone should be controlled so that the particle drying occurs sufficiently rapidly to result in the surface collapse and convolution without preceding so rapidly that the particle fractures.

In still another specific aspect of the method of the present invention, the dried particles are collected by separating substantially the entire particle output of the drying step from the gas stream. It has been found that proper control of the atomization and drying conditions can produce a dried powder having at least 90% of the mass of particles in the size range from 0.1 μm to 7 μm, more preferably having at least 95% in the size range from 0.4 μm to 5 μm, thus permitting the output of the drying step to be collected and the powder used without the need to size classify the product prior to packaging. The collected powder may then be used in any conventional manner for powder pharmaceuticals. Usually, a portion of the particle output will be packaged in a suitable container, such as a unit dosage container useful in dry powder inhalers.

In yet another specific aspect of the method of the present invention, the powder separation step will comprise passing the entire gas stream through a separator, where the separator removes at least about 90% by weight of all particles having the size of 1 μm from the gas stream. The separator may comprise a high efficiency cyclone specifically designed and operated under conditions resulting in the requisite high removal efficiency for the ultrafine particles produced by the method of the present invention. Alternatively, the separator may comprise filter elements, such as a sintered metal fiber filter, a membrane filter, (e.g, a bag filter), or the like.

The methods of the present invention are useful for producing dry powders of biological macromolecules, typically macromolecules which are suitable for pharmaceutical uses, i.e., as drugs for human and veterinary purposes. Biological macromolecules include proteins, polypeptides, oligopeptides, high molecular weight polysaccharides (typically having a molecular weight above 2 kD), nucleic acids, and the like. Particular biological macromolecules are set forth in Table 1 below. The method is particularly useful for producing dry powders of insulin, which is a polypeptide hormone having a molecular weight of about 7.5 kD or above. Insulin powders prepared according to the present invention may be derived from animal sources, such as bovine insulin, or may be prepared recombinantly. Recombinant insulins may have an amino acid sequence identical to that of natural human insulin, or may be modified to some extent while maintaining the desired insulin activity.

Compositions according to the present invention comprise dispersible macromolecule powders intended for pulmonary delivery, i.e., inhalation by a patient into the alveolar regions of the patient's lungs. The compositions comprises particles having an average particle size below 10 μm and a rugosity above 2, preferably being above 3, and sometimes being above 5, usually being in the range from 2-6, preferably being in the range from 3-6, and sometimes being in the range from 4-6. Preferably, the particles of the composition will have a moisture content below 5% by weight, more preferably below 3% by weight, and typically below 2% by weight. Rugosity may be measured by BET or other conventional particle surface analysis techniques. Preferably, 90% by weight of the compositions will comprise particles having a particle size in the range from 0.1 μm to 7 μm, more preferably 95% in the range from 0.4 μm to 5 μm. The compositions will often be packaged as unit doses where a therapeutically effective amount of the composition is present in a unit dose receptacle, such as a blister pack, gelatin capsule, or the like.

DETAILED DESCRIPTION

Figure 1:
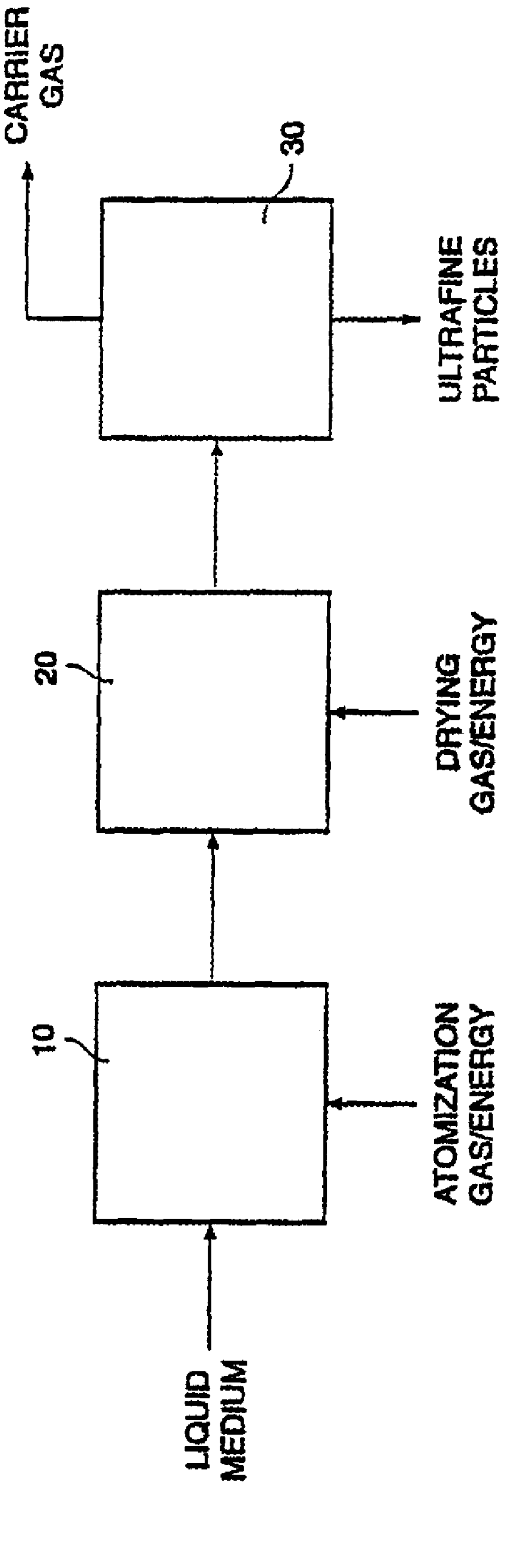
FIG. 1 is a block diagram illustrating the primary unit operations of the methods of the present invention.

The present invention relates to the methods for preparing compositions comprising ultrafine dry powder of biological macromolecules intended primarily for pulmonary delivery to patients for a variety of therapeutic and clinical purposes where a first primary aspect of the invention relates to control of powder characteristics which enhance use of the powders for the intended purposes. A second primary aspect of the present invention relates to the compositions themselves as well as packaged compositions, particularly including unit dosage forms of the compositions. A third primary aspect of the present invention relates to the capacity of the demonstrated process to produce powders with the desired characteristics at a scale that can support market requirements of a given drug.

The term "biological macromolecule" is intended to include known and future biological compounds having therapeutic and other useful activities. The biological macromolecules will typically be proteins, polypeptides, oligopeptides, nucleic acids, and relatively high weight polysaccharides, and the methods of the present invention can reform such compounds into ultrafine dry powders having desirable characteristics, particularly for pulmonary delivery. Some examples of biological macromolecules suitable for preparation as ultrafine dry powders according to the method of the present invention are set forth in Table 1 below. Such biological macromolecules will initially be solubilized, suspended, or otherwise dispersed in an evaporable liquid medium which is then atomized, dried, and collected according to the method of the present invention. Preferred biological macromolecules include insulin, interleukin-1 receptor, parathyroid hormone (PTH-34), alpha-1 antitrypsin, calcitonin, low molecular weight heparin, heparin, interferon, and nucleic acids. A detailed example for the preparation of insulin compositions using the methods of the present invention is set forth in the Experimental section below.

TABLE 1

| EXEMPLARY BIOLOGICAL MACROMOLECULE DRUGS | |
|---|---|
| DRUG | INDICATIONS |
| Calcitonin | Osteoporosis Prophylaxis<br>Paget's Disease<br>Hypercalcemia |
| Erythropoietin (EPO) | Anemia |
| Factor IX | Hemophilia B |
| Granulocyte Colony Stimulating Factor (G-CSF) | Neutropenia |
| Granulocyte Macrophage Colony Stimulating Factor (GM-CSF) | Bone Marrow Engraftment/ Transplant Failure |
| Growth Hormone | Short Stature<br>Renal Failure |
| Heparin | Blood Clotting<br>Asthma |
| Heparin (Low Molecular Weight) | Blood Clotting |
| Insulin | Type I and Type II Diabetes |
| Interferon Alpha | Hepatitis B and C<br>Hairy Cell Leukemia<br>Kaposi's Sarcoma |
| Interferon Beta | Multiple Sclerosis |
| Interferon Gamma | Chronic Granulomatous Disease |
| Interleukin-2 | Renal Cancer |
| Luteinizing Hormone Releasing Hormone (LHRH) | Prostate Cancer<br>Endometriosis |
| Somatostatin Analog | Gastrointestinal Cancers |
| Vasopressin Analog | Diabetes Insipidus<br>Bed Wetting |
| Follicle Stimulating Hormone (FSH) | Fertility |
| Amylin | Type I Diabetes |
| Ciliary Neurotrophic Factor | Lou Gehrig's Disease |
| Growth Hormone Releasing Factor (GRF) | Short Stature |
| Insulin-Like Growth Factor | Osteoporosis<br>Nutritional Support |
| Insulinotropin | Type II Diabetes |
| Interferon Beta | Hepatitis B and C |
| Interferon Gamma | Rheumatoid Arthritis |
| Interleukin-1 Receptor Antagonist | Rheumatoid Arthritis |
| Interleukin-3 | Adjuvant to Chemotherapy |
| Interleukin-4 | Immunodeficiency Disease |
| Interleukin-6 | Thrombocytopenia |
| Macrophage Colony Stimulating Factor (M-CSF) | Fungal Disease<br>Cancer<br>Hypercholesterolemia |
| Nerve Growth Factor | Peripheral Neuropathies |
| Parathyroid Hormone | Osteoporosis |
| Somatostatin Analog | Refractory Diarrheas |
| Thymosin Alpha 1 | Hepatitis B and C |
| IIb/IIIa Inhibitor | Unstable Angina |
| Alpha-1 Antitrypsin | Cystic Fibrosis |
| Anti-RSV Antibody | Respiratory Syncytial Virus |
| Cystic Fibrosis Transmembrane Regulator (CFTR) Gene | Cystic Fibrosis |
| Deoxyribonuclease (DNase) | Chronic Bronchitis |
| Bactericidal/Permeability Increasing Protein (BPI) | Adult Respiratory Distress Syndrome (ARDS) |
| Anti-CMV Antibody | Cytomegalovirus |
| Interleukin-1 Receptor | Asthma |
| Interleukin-1 Receptor Antagonist | Asthma |

The phrase "ultrafine dry powder" means a powder composition comprising a plurality of discrete, dry particles having the characteristics set forth below. In particular, the dry particles will have an average particle size below 5 μm, more preferably being in the range from 0.4-5 μm, preferably from 0.4-4 μm, and most preferably from 0.4-3 μm. The average particle size of the powder will be measured as mass mean diameter (MMD) by conventional techniques. A particular powder sizing technique uses a centrifugal sedimentary particle size analyzer (Horiba Capa 700). The powders will be capable of being readily dispersed in an inhalation device and subsequently inhaled by a patient so that the particles are able to penetrate into the alveolar regions of the lungs.

Of particular importance to the present invention, the ultrafine dry particle compositions produced by the method will have particle size distributions which enable them to target the alveolar region of the lung for pulmonary delivery of systemically acting proteins. Such compositions advantageously may be incorporated into unit dosage and other forms without further size classification. Usually, the ultrafine dry powders will have a size distribution where at least 90% of the powder by weight will comprise particles having an average size in the range from 0.1 μm to 7μm, with preferably at least 95% being in the range from 0.4 μm to 5 μm. Additionally, it is desirable that the particle size distribution avoid having an excess amount of particles with very small average diameters, i.e., below 0.4 μm.

Conversely, known powders of therapeutic compounds that are inhaled for the treatment of asthma and chronic bronchitis need to be delivered more centrally in the airways (i.e., not to the alveolar regions). These powders can produce an aerosol with a significantly larger particle size distribution having a mean diameter between 3 and 10 μm. Powders of this size are collected more readily in high yield in conventional spray driers, than the powders having the optimal particle size for pulmonary delivery.

The term "dry" means that the particles of the powder have a moisture content such that the powder is physically and chemically stable in storage at room temperature and is readily dispersible in an inhalation device to form an aerosol. Usually, the moisture content of the particles is below 10% by weight water, usually being below 5% by weight, preferably being below 3% by weight, more preferably being below 2% by weight, and optionally being below about 1% by weight or lower. The moisture content will usually be controlled by the drying conditions, as described in more detail below.

The term "dry" means that the particles of the powder have a moisture content such that the powder is readily dispersible in an inhalation device to form an aerosol. Usually, the moisture content of the particles is below 10% by weight water, usually being below 5% by weight, preferably being below 3% by weight, more preferably being below 2% by weight, and optionally being below about 1% by weight or lower. The moisture content will usually be controlled by the drying conditions, as described in more detail below. In some cases, however, non-aqueous medium may be used for dispersing the biological macromolecules, in which case the aqueous content may approach zero.

The term "therapeutically effective amount" is the amount present in the composition that is needed to provide the desired level of drug in the subject to be treated to give the anticipated physiological response. This amount is determined for each drug on a case-by-case basis. The term "physiologically effective amount" is that amount delivered to a subject to give the desired palliative or curative effect. This amount is specific for each drug and its ultimate approved dosage level.

The therapeutically effective amount of active pharmaceutical will vary in the composition depending on the biological activity of the biological macromolecule employed and the amount needed in a unit dosage form. Because the subject powders are dispersible, it is highly preferred that they be manufactured in a unit dosage form in a manner that allows for ready manipulation by the formulator and by the consumer. This generally means that a unit dosage will be between about 0.5 mg and 15 mg of total material in the dry powder composition, preferably between about 2 mg and 10 mg. Generally, the amount of macromolecule in the composition will vary from about 0.05% w to about 99.0% w. Most preferably the composition will be about 0.2% to about 97.0% w macromolecule.

A pharmaceutically acceptable carrier may optionally be incorporated into the particles (or as a bulk carrier for the particles) to provide the stability, dispersibility, consistency and/or bulking characteristics to enhance uniform pulmonary delivery of the composition to a subject in need thereof. The term "pharmaceutically acceptable carrier" means that the carrier can be taken into the lungs with no significant adverse toxicological effects on the lungs. Numerically the amount may be from about 0.05% w to about 99.95% w, depending on the activity of the drug being employed. Preferably about 5% w to about 95% w will be used.

Such pharmaceutically acceptable carriers may be one or a combination of two or more pharmaceutical excipients, but will generally be substantially free of any "penetration enhancers." Penetration enhancers are surface active compounds which promote penetration of a drug through a mucosal membrane or lining and are proposed for use in intranasal, intrarectal, and intravaginal drug formulations. Exemplary penetration enhancers include bile salts, e.g., taurocholate, glycocholate, and deoxycholate; fusidates, e.g., taurodehydrofusidate; and biocompatible detergents, e.g., Tweens, Laureth-9, and the like. The use of penetration enhancers in formulations for the lungs, however, is generally undesirable because the epithelial blood barrier in the lung can be adversely affected by such surface active compounds. The dry powder compositions of the present invention are readily absorbed in the lungs without the need to employ penetration enhancers.

The types of pharmaceutical excipients that are useful as carriers in this invention include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

It has been found that HSA is particularly valuable as a carrier in that it provides improved dispersibility.

Bulking agents which may be combined with the powders of the present invention include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-β-cyclodextrin; and polysaccharides, such as raffinose, maltodextrins, dextrans, and the like; alditols, such as mannitol, xylitol, and the like. A preferred group of carbohydrates includes lactose, trehalose, raffinose maltodextrins, and mannitol. Suitable polypeptides include aspartame. Amino acids include alanine and glycine, with glycine being preferred.

Additives, which are minor components of the composition of this invention, may be included for conformational stability during spray drying and for improving dispersibility of the powder. These additives include hydrophobic amino acids such as tryptophan, tyrosine, leucine, phenylalanine, and the like.

Suitable pH adjusters or buffers include organic salts prepared from organic acids and bases, such as sodium citrate, sodium ascorbate, and the like; sodium citrate is preferred.

The methods of the present invention have been found to provide particles which are dispersible and which further resist agglomeration and undesirable compaction during handling and packaging operations. A particular characteristic which has been found to relate directly to such improved dispersibility and handling characteristics is the product rugosity. Rugosity is the ratio of the specific area (as measured by BET, molecular surface adsorption, or other conventional technique) and the surface area calculated from the particle size distribution (as measured by centrifugal sedimentary particle size analyzer, Horiba Capa 700) and particle density (as measured by pycnometry), assuming non-porous spherical particles. If the particles are known to be generally nodular in shape, as is the case in spray drying, rugosity is a measure of the degree of convolution or folding of the surface. This may be verified for powders made by the present invention by SEM analysis. A rugosity of 1 indicates that the particle surface is spherical and non-porous. Rugosity values greater than 1 indicate that the particle surface is non-uniform and convoluted to at least some extent, with higher numbers indicating a higher degree of non-uniformity. For the powders of the present invention, it has been found that particles preferably have a rugosity of at least 2, more preferably being at least 3, usually being in the range from 2-6, preferably being in the range from 3-6, and more preferably being in the range from 4-6.

Unit dosage forms for pulmonary delivery of dispersible dry powder biological macromolecules comprise a unit dosage receptacle containing a dry powder as described above. The powder is placed within a suitable dosage receptacle in an amount sufficient to provide a subject with drug for a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522 issued Oct. 14, 1980; U.S. Pat. No. 4,192,309 issued Mar. 11, 1980; and U.S. Pat. No. 4,105,027 issued Aug. 8, 1978. Suitable containers also include those used in conjunction with Glaxo's Ventolin Rotohaler brand powder inhaler or Fison's Spinhaler brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). Preferred dry powder inhalers are those described in U.S. patent application Ser. No. 08/309,691, now U.S. Pat. No. 5,785,049, and Ser. No. 08/487,184, now U.S. Pat. No. 5,740,794, assigned to the assignee of the present invention. The latter application has been published as WO 96/09085.

Referring now to FIG. 1, processes according to the present invention for preparing dispersible dry powders of biological macromolecules comprise an atomization operation 10 which produces droplets of a liquid medium which are dried in a drying operation 20. Drying of the liquid droplets results in formation of the discrete particles which form the dry powder compositions which are then collected in a separation operation 30. Each of these unit operations will be described in greater detail below.

The atomization process 10 may utilize any one of several conventional forms of atomizers. The atomization process increases the surface area of the starting liquid. This requires an increase in the surface energy of the liquid, the magnitude of which is directly proportional to the area increase, which in turn, is inversely proportional to the square of the diameter of the droplets. The source of this energy increase depends on the type of atomizer used. Any atomizer (centrifugal, sonic, pressure, two fluid) capable of producing droplets with a mass median diameter of less than about 11 μm could be used. Preferred for the present invention is the use of two fluid atomizers where the liquid medium is delivered through a nozzle concurrently with a high pressure gas stream. Particularly preferred is the use of two-fluid atomization nozzles as described in more detail below which is capable of producing droplets having a median diameter less than 10 μm.

The atomization gas will usually be air which has been filtered or otherwise cleaned to remove particulates and other contaminants. Alternatively, other gases, such as nitrogen may be used. The atomization gas will be pressurized for delivery through the atomization nozzle, typically to a pressure above 25 psig, preferably being above 50 psig. Although flow of the atomization gas is generally limited to sonic velocity, the higher delivery pressures result in an increased atomization gas density. Such increased gas density has been found to reduce the droplet size formed in the atomization operation. Smaller droplet sizes, in turn, result in smaller particle sizes. The atomization conditions, including atomization gas flow rate, atomization gas pressure, liquid flow rate, and the like, will be controlled to produce liquid droplets having an average diameter below 11 μm as measured by phase doppler velocimetry. In defining the preferred atomizer design and operating conditions, the droplet size distribution of the liquid spray is measured directly using Aerometric's Phase Doppler Particle Size Analyzer. The droplet size distribution may also be calculated from the measured dry particle size distribution (Horiba Capa 700) and particle density. The results of these two methods are in good agreement with one another. Preferably, the atomized droplets will have an average diameter in the range from 5 μm to 11 μm, more preferably from 6 μm to 8 μm. The gas:liquid mass flow ratio is preferably maintained above 5, more preferably being in the range from 8 to 10. Control of the gas:liquid mass flow ratio within these ranges is particularly important for control of the particle droplet size.

Heretofore, it had been generally thought that conventional atomization equipment for spray driers was not suitable for producing the very fine droplets (>11 μm) used in the present invention. See, e.g. Masters, Handbook of Spray Drying, 4th ed., Wiley & Sons 1985. It has been found, however, that operation of two fluid nozzles within the parameters set forth above can reliably achieve spray droplets in the desired size range.

The liquid medium may be a solution, suspension, or other dispersion of the biological macromolecule in a suitable liquid carrier. Preferably, the biological macromolecule will be present as a solution in the liquid solvent in combination with the pharmaceutically acceptable, and the liquid carrier will be water. It is possible, however, to employ other liquid solvents, such as organic liquids, ethanol, and the like. The total dissolved solids (including the macromolecule and other carriers, excipients, etc., that may be present in the final dried particle) may be present at a wide range of concentrations, typically being present at from 0.1% by weight to 10% by weight. Usually, however, it will be desirable to maximize the solids concentration that produces particles in the inhalation size range and has the desired dispersibility characteristics, typically the solids concentration ranges from 0.5% to 10%, preferably from 1.0% to 5%. Liquid media containing relatively low concentrations of the biological macromolecule will result in dried particulates having relatively small diameters as described in more detail below.

The drying operation 20 will be performed next to evaporate liquid from the droplets produced by the atomization operation 10. Usually, the drying will require introducing energy to the droplets, typically by mixing the droplets with a heated gas which causes evaporation of the water or other liquid medium. Preferably, the mixing is done in a spray dryer or equivalent chamber where a heated gas stream has been introduced. Preferably, the heated gas stream will flow concurrently with the atomized liquid, but it would also be possible to employ counter-current flow, cross-current flow, or other flow patterns.

The drying operation is controlled to provide dried particles having particular characteristics, such as a rugosity above 2, as discussed above. Rugosities above 2 may be obtained by controlling the drying rate so that a viscous layer of material is rapidly formed on the exterior of the droplet. Thereafter, the drying rate should be sufficiently rapid so that the moisture is removed through the exterior layer of material, resulting in collapse and convolution of the outer layer to provide a highly irregular outer surface. The drying should not be so rapid, however, that the outer layer of material is ruptured. The drying rate may be controlled based on a number of variables, including the droplet size distribution, the inlet temperature of the gas stream, the outlet temperature of the gas stream, the inlet temperature of the liquid droplets, and the manner in which the atomized spray and hot drying gas are mixed. Preferably, the drying gas stream will have an inlet temperature of at least 90° C., more preferably being within the ranges set forth above. The outlet temperature will usually be at least about 70° C., preferably in the ranges set forth above. The drying gas will usually be air which has been filtered or otherwise treated to remove particulates and other contaminants. The air will be moved through the system using conventional blowers or compressors.

The separation operation 30 will be selected in order to achieve very high efficiency collection of the ultrafine particles produced by the drying operation 20. Conventional separation operations may be used, although in some cases they should be modified in order to assure collection of sub-micron particles. In an exemplary embodiment, separation is achieved using a filter medium such as a membrane medium (bag filter), a sintered metal fiber filter, or the like. Alternatively, and often preferably, separation may be achieved using cyclone separators, although it is usually desirable to provide for high energy separation in order to assure the efficient collection of sub-micron particles. The separation operation should achieve collection of at least 80% of all particles above 1 μm in average particle size, preferably being above 85%, more preferably being above 90%, and even more preferably being above 95%, in collection efficiency.

In some cases, a cyclone separator can be used to separate very fine particles, e.g. 0.1 μm, from the final collected particles. The cyclone operating parameters can be selected to provide an approximate cutoff where particles above about 0.1 μm are collected while particles below 0.1 μm are carried over in the overhead exhaust. The presence of particles below 0.1 μm in the pulmonary powder is undesirable since they will generally not deposit in the alveolar regions of the lungs, but instead will be exhaled.

A particular advantage of the method of the present invention is that all of the particles produced in the drying operation and collected in the separation operation may be used for packaging in the desired pharmaceutical packages without the need to further separate or classify the particles into desired size ranges. This result is a combination of the atomization and drying conditions which produce an ultrafine dry powder composition having individual particles sized within the ranges desirable for pulmonary delivery. Thus, the separation operation 30 need only separate the particles from the drying gas stream (with an optional 0.4 μm cutoff), where separation is achieved at as high an efficiency as possible since substantially all of the collected material is suitable for use in the pharmaceutical formulations.

Figure 2:
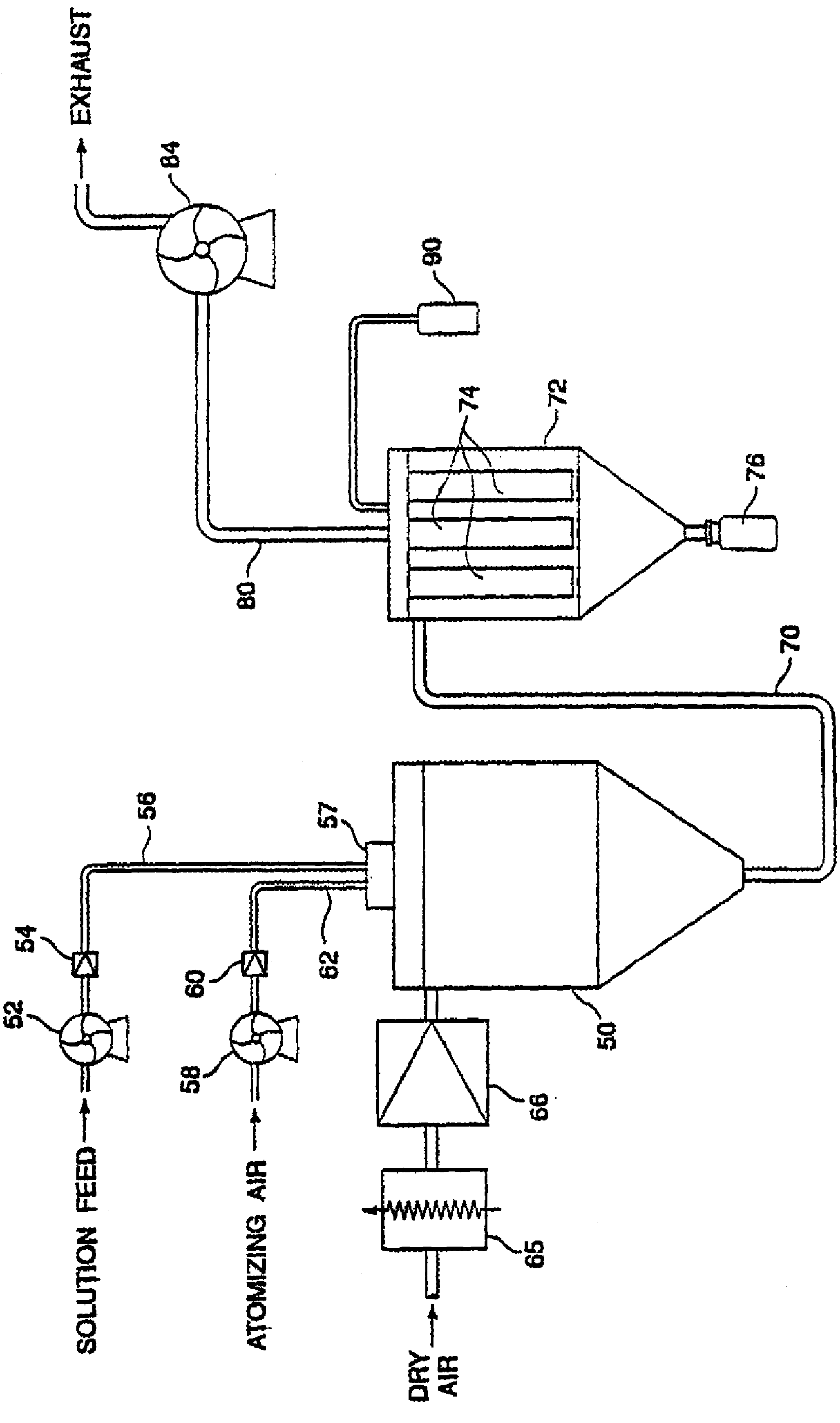
FIG. 2 is a more detailed flowchart illustrating a system suitable for performing an exemplary method according to the present invention

Referring now to FIG. 2, an exemplary process flow diagram for performing the method of the present invention will be described. The process flow diagram includes a spray dryer 50, which may be a commercial spray dryer (adapted for the method of the present invention) such as those available from suppliers such as Buchi, Niro, APV, Yamato Chemical Company, Okawara Kakoki Company, and others. The spray dryer is fed a solution of the liquid medium (solution feed) described above through a supply pump 52, filter 54, and supply line 56. The supply line 56 is connected to a two-fluid atomization nozzle 57, as described below in connection with FIG. 3. Atomizing air is supplied from a compressor 58, a filter 60, and line 62 to the nozzle 57. Drying air is also provided to the spray dryer 50 through a heater 65 and a filter 66.

Dried particles from the spray dryer 50 are carried by the air flow through conduit 70 to a filter housing 72. The filter housing 72 includes a plurality of internal filter elements 74, which may be bag filters or sintered metal fiber filters, such as sintered stainless steel fiber filters of the type described in Smale, Manufacturing Chemist, p. 29, April 1992. Alternative filter media comprise bag filters, cloth filters, and cartridge filters. In all cases, the gas stream carrying the dried particles will flow into the shell of separator housing 72, and the carrier gas will pass through the filter elements 74. Passage of the dried particles, however, will be blocked by the filter elements, and the dried particles will fall by gravity to the bottom of the housing 72 where they will be collected in a particle collection canister 76. The canister 76 may periodically be removed and replaced, and the dry powder in the canister utilized for packaging in unit dosage or other forms. The carrier gas will pass out from the top of the separator housing 72 through line 80 and an exhaust fan 84. The filters 82 will collect any particles which may inadvertently pass through the filter media 74. A source 90 of high pressure gas is provided for periodically producing a pulsed flow of counter-current air through the filter media 74. Such pulsed air flow in the reverse direction will dislodge particles which adhere to the inlet side of the filter medium to prevent caking. An exemplary system for the production of an insulin powder according to the method of the present invention and employing a process flow according to FIG. 2 is presented in the Experimental section below.

Figure 3:
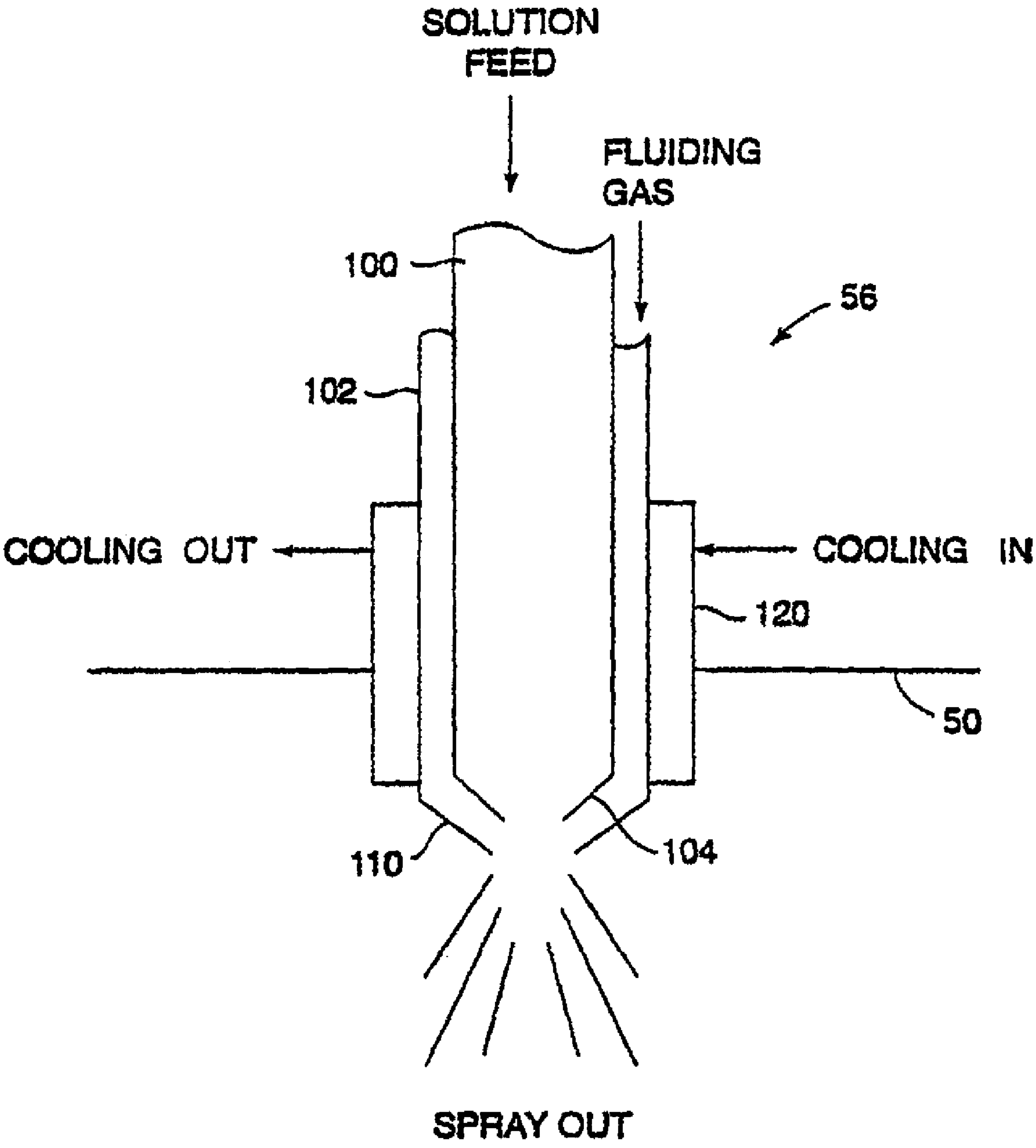
FIG. 3 is a schematic illustration depicting a preferred atomization nozzle useful for performing the atomization step of the method of the present invention.

Referring now to FIG. 3, an exemplary two-fluid nozzle is illustrated. Flow line 56 includes an inner conduit 100 and outer conduit 102. The inner conduit 100 carries the solution feed and terminates in an orifice 104 having a diameter in the range from 0.015 in. to 0.075 in., preferably from 0.025 to 0.05 in. depending on the liquid flow rate. The outer conduit 102 is disposed coaxially about the inner conduit 100 and carries the atomizing gas from line 62. Conduit 62 terminates in an orifice 110 which is concentric about the orifice 104 of conduit 100. The diameter of orifice 110 is typically larger than that of orifice 104, usually having a cross-sectional area which is sufficient to produce the desired mass flow rate of air with the desired upstream pressure.

Optionally, a cooling jacket 120 may be provided about the spray nozzle (or between the atomizing gas and the solution feed) to maintain a relatively low temperature of the solution feed when the solution feed enters the spray dryer 50. The cooling jacket 120 will typically carry cooling water at a temperature and in an amount sufficient to maintain the solution feed temperature below a level at which the biological macromolecule might be degraded, usually from 4° C. to 45° C. Cooling will generally be necessary only with heat sensitive macromolecules. Higher solution feed temperatures result in lower viscosity, where the lower viscosity can reduce the droplet size which is formed by the atomization operation.

Figure 4:
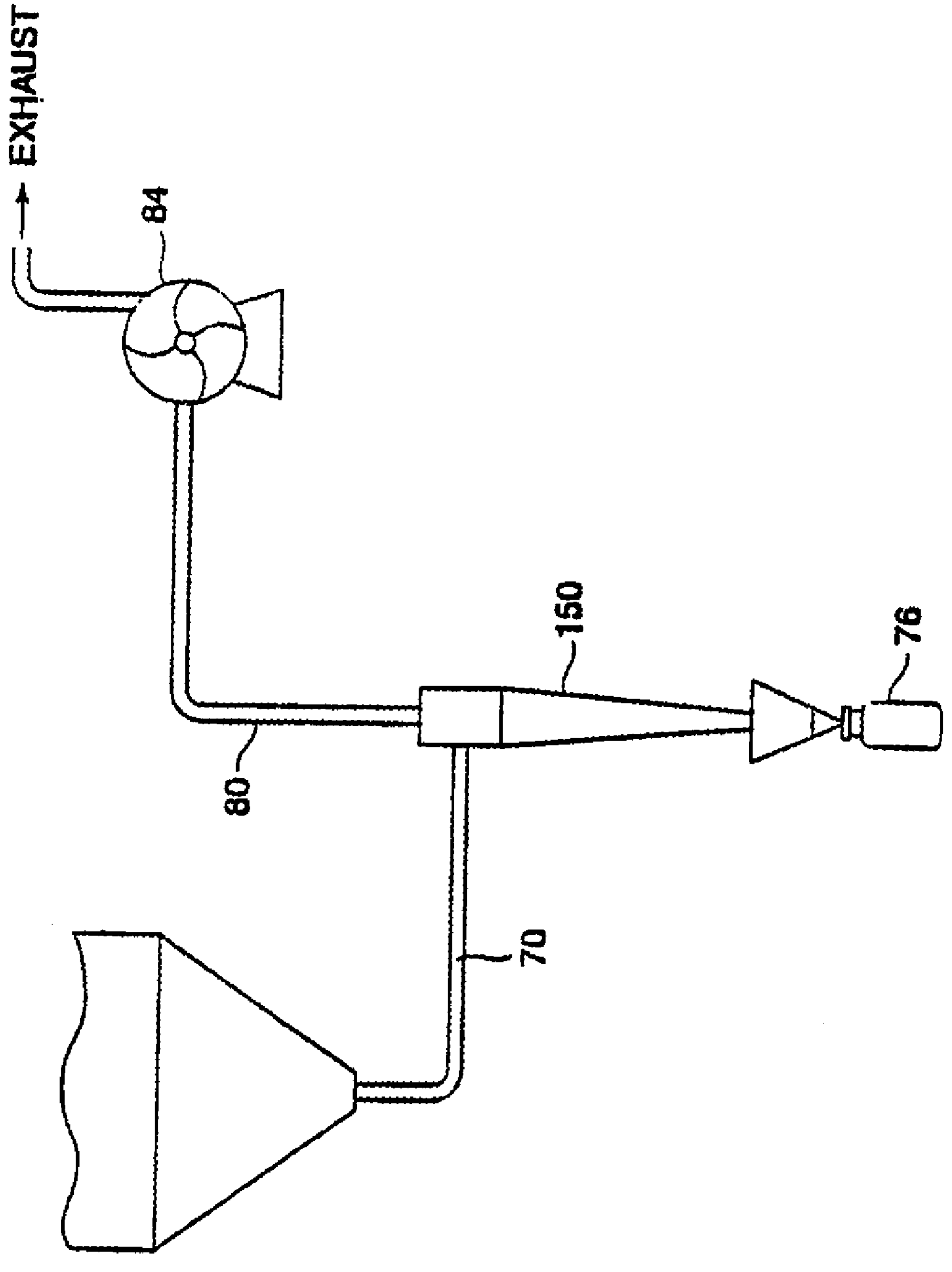
FIG. 4 illustrates alternative apparatus for the system of FIG. 2 for performing the separation step of the method of the present invention.

Referring now to FIG. 4, as an alternative to use of a filter separator 72, as illustrated in FIG. 2, the collection operation may be performed by a cyclone 150. The cyclone 150 will receive the dried particles through conduit 70 and the carrier gas will pass upwardly through line 80, in a manner analogous to that illustrated in FIG. 2. The cyclone 150 will be designed and operated in a manner to assure very high collection efficiencies of the ultrafine particles produced by the method of the present invention. The use of a cyclone will result in some carry over of extremely fine particles through the overhead outlet 80. While in some cases this may be undesirable, the further separation may be relied on to remove particles which are too small to reach the alveolar regions of the lung, e.g. below 7 μm.

The following examples are offered by way of illustration, not by way of limitation.

EXPERIMENTAL

Example 1

The spray drying equipment configuration is shown in FIGS. 2 and 4. A total of 20 liters of solution was processed during the run. The solution contained 250 grams (1.25% wt.) of total solids, 20% of which was insulin. The balance of the solids was a mixture of mannitol, sodium citrate and glycine. The solution was fed to the atomizer at 4° C. at a rate of about 44 ml/min using a Watson Marlow peristaltic pump and silicone tubing. The actual feed rate was controlled by a PID loop using the spray dryer outlet temperature as the control variable. The atomizer temperature control circulation jacket had 4° C. water circulated through it. The atomizer air was flow controlled and measured using a needle valve and glass rotameter at 12 scfm and 38 psig. Both the air and liquid flows passed through polishing filters just prior to entering the atomizer (Millipak 60 and Millipore Wafergard II F-40 In line gas filters). The powder was collected in a high efficiency cyclone operated at a pressure drop of 55 inches H2O. The drying air flow rate was controlled by an AC speed control system on the blower drive motor at 100 scfm and was measured at the discharge of the blower using an orifice plate and differential pressure transducer. The drying air temperature was controlled at 130° C. on a time proportioning PID loop and the 7.5 KW heater. A total of 225 grams of powder was recovered in four separate collectors giving a total yield of 90%. The powder in each collector was analyzed as shown in Table 2.

TABLE 2

| Attribute/Method | Units | Collector 1 | Collector 2 | Collector 3 | Collector 4 |
|---|---|---|---|---|---|
| Moisture/Karl Fisher | $H_2O$ % wt. | 3.4% | 2.8% | 2.8% | 3.0% |
| Particle size/Horiba | MMD | 1.8 μm | 1.4 μm | 1.6 μm | 1.4 μm |
| Capa 700 | % < 5 micron | 100 | 100 | 100 | 100 |
| Aerosol particle size/ Cascade impactor | MMAD | 3.3 μm 68% | ND | ND | ND |
| Delivered Dose Efficiency Inhale device/gravimetric | % ± SD | 83 ± 3 | 84 ± 5 | 84 ± 4 | 81 ± 6 |
| Surface Area | $m^2/g$ | 11.3 | 11.7 | ND | ND |
| Rugosity | | 3.8 | 3.9 | ND | ND |

Example 2

A total of 2.4 liters of solution was processed. The solution contained 100 grams (4.0% wt.) of total solids, 20% of which was insulin. The balance of the solids was a mixture of mannitol, sodium citrate and glycine. The spray dryer used in Experiment 1 was used for this experiment. The solution was fed to the atomizer at 4° C. at a rate varying with outlet temperature using a Watson Marlow peristaltic pump and silicone tubing. The actual feed rate was controlled by a PID loop using the spray dryer outlet temperature as the control variable. The atomizer temperature control circulation jacket had 45° C. water circulated through it. The atomizer air was flow controlled and measured using a needle valve and glass rotameter at 13.8 scfm and 70 psig. Both air and liquid flows passed through polishing filters just prior to entering the atomizer (Millipak 60 and Millipore Wafergard II F-40 In line gas filters). The drying air flow rate was controlled by an AC speed control system on the blower drive motor at 95 scfm and was measured at the discharge of the blower using an orifice plate and differential pressure transducer. The drying air temperature was controlled at 150° C. on a time proportioning PID loop and the 7.5 KW heater. Drying outlet air was varied from 70, 75, and 80° C. The powder collectors were exchanged for each temperature setpoint. The powder in each collector was analyzed as shown in Table 3.

TABLE 3

| Attribute/Method | Units | Collector 1 Inlet Air 70° C. | Collector 2 Inlet Air 75° C. | Collector 3 Inlet Air 80° C. |
|---|---|---|---|---|
| Moisture Karl Fisher | $H_2O$ % wt. | 2.28 | 2.02 | 1.63 |
| Particle size, | MMD | 2.41 μm | 2.69 μm | 2.43 μm |
| Horiba Capa 700 | % < 5 micron | 100 | 82.3 | 100 |
| Delivered Dose Eff. | % ± SD | 71 ± 3 | 73 ± 3 | 71 ± 2 |
| Mean Surface Area Micrometrics Gemini | $m^2/g$ ± SD | 6.76 ± .19 | 6 ± .02 | 8.07 ± .12 |
| Rugosity | | 3.6 | 3.9 | 3.8 |

Example 3

The spray dryer was reconfigured with a bag house outfitted with sintered stainless steel fiber filter elements (Fairey Microfiltrex). The equipment configuration is shown in FIG. 2.

A total of 8 liters of solution was processed during the insulin run. The solution contained 100 grams (1.25% wt.) of total solids, 20% of which was insulin. The balance of the solids was a mixture of mannitol, sodium citrate and glycine. The solution was fed to the atomizer at 4° C. at a rate of 55 ml/min using a Watson Marlow peristaltic pump and silicone tubing. The atomizer temperature control circulation jacket had 4° C. water circulated through it. The atomizer air was flow controlled and measured using a needle valve and glass rotameter at 12 scfm and 42 psig. Both air and liquid flows passed through polishing filters just prior to entering the atomizer (Millipak-60, and Millipore Wafergard II F-40 In line Gas Filter). The drying air flow rate was controlled by an AC speed control system on the blower drive motor at 100 scfm and was measured at the discharge of the blower using an orifice plate and differential pressure transducer. The drying air temperature was controlled at 145° C. on the Niro 7.5 KW heater. Particle collection was carried out on a modified Pacific Engineering (Anaheim, Calif.) self-cleaning chamber (bag house or filter housing). The bag house was brought in house and modified to allow the number of filters to be varied. Cage and fabric filters were replaced with two Fairey Microfiltrex (Hampshire, UK) sintered metal fiber filter. A system for reverse pulsing (back flushing the bags with high pressure air) the filter elements was built into the top of the bag house to aid in recovery. The pulse was activated for less then one second every 20 seconds. Pulse pressure was 110 psig. Powder dropped to the bottom of the bag house under gravity and mechanical aid (shaking). The powder in the collector was analyzed as shown in Table 4.

TABLE 4

| Attribute/Method | Units | Collector |
|---|---|---|
| Moisture<br>Karl Fisher | $H_2O$ % wt. | 4.8% |
| Particle size,<br>Horiba Capa 700 | MMD | 1.34 μm |
| | % < 5 micron | 100% |
| | % < 1.4 micron | 62% |
| | % < 1.0 | 44% |
| Delivered Dose Eff.<br>Dry Powder device | % ± SD | 73 ± 2 |

Although the foregoing invention has been described in some detail by way of illustration and example, for purposes of clarity of understanding, it will be obvious that certain changes and modifications may be practiced within the scope of the appended claims.

What is claimed is:

1. A composition comprising:

a plurality of inhalable particles, each comprising insulin and a pharmaceutically acceptable carrier, wherein the inhalable particles have a rugosity of at least 2, as determined by air permeametry and wherein the composition has an average particle size of less than 10 μm.

2. The composition of claim 1, wherein the rugosity is at least 3.

3. The composition of claim 1, wherein the rugosity ranges from 2 to 6.

4. The composition of claim 1, wherein the rugosity ranges from 4 to 6.

5. The composition of claim 1, wherein the pharmaceutically acceptable carrier comprises a buffer.

6. The composition of claim 5, wherein the buffer comprises sodium citrate.

7. The composition of claim 1, wherein the pharmaceutically acceptable carrier comprises a penetration enhancer.

8. The composition of claim 1, wherein the particles have a moisture content of less than 10 wt %.

9. The composition of claim 1, wherein the particles have a moisture content of less than 5 wt %.

10. The composition of claim 1, wherein the composition has an average particle size of less than 5 μm.

11. The composition of claim 1, wherein the rugosity is at least 3, and wherein the particles have a moisture content of less than 10 wt %.

12. The composition of claim 1, wherein the rugosity is at least 3, wherein the composition further comprises sodium citrate, and wherein the particles have a moisture content of less than 10 wt %.

13. The composition of claim 1, wherein the rugosity is at least 3, wherein the composition further comprises a penetration enhancer, and wherein the particles have a moisture content of less than 10 wt %.

14. A unit dosage, comprising a therapeutically effective amount of the composition of claim 1 within a receptacle.

15. The unit dosage of claim 14, wherein the receptacle comprises a capsule.

16. The unit dosage of claim 14, wherein the receptacle comprises a foil plastic laminate.

17. A unit dosage, comprising between about 0.5 mg and 15 mg of the composition of claim 1 within a receptacle.

18. An inhalation device, wherein the receptacle of claim 14 is within the inhalation device.

19. A composition comprising:

a plurality of inhalable particles, each comprising insulin and a pharmaceutically acceptable carrier, wherein the inhalable particles have a rugosity of at least 2, as determined by BET, centrifugal sedimentary particle size analysis, and pycnometry, and wherein the composition has an average particle size of less than 10 μm.

20. The composition of claim 19, wherein the rugosity is at least 3.

21. The composition of claim 19, wherein the rugosity ranges from 2 to 6.

22. The composition of claim 19, wherein the rugosity ranges from 4 to 6.

23. The composition of claim 19, wherein the pharmaceutically acceptable carrier comprises a buffer.

24. The composition of claim 23, wherein the buffer comprises sodium citrate.

25. The composition of claim 19, wherein the pharmaceutically acceptable carrier comprises a penetration enhancer.

26. The composition of claim 19, wherein the particles have a moisture content of less than 10 wt %.

27. The composition of claim 19, wherein the particles have a moisture content of less than 5 wt %.

28. The composition of claim 19, wherein the composition has an average particle size of less than 5 μm.

29. The composition of claim 19, wherein the rugosity is at least 3, and wherein the particles have a moisture content of less than 10 wt %.

30. The composition of claim 19, wherein the rugosity is at least 3, wherein the composition further comprises sodium citrate, and wherein the particles have a moisture content of less than 10 wt %.

31. The composition of claim 19, wherein the rugosity is at least 3, wherein the composition further comprises a penetration enhancer, and wherein the particles have a moisture content of less than 10 wt %.

32. A unit dosage, comprising a therapeutically effective amount of the composition of claim 19 within a receptacle.

33. The unit dosage of claim 32, wherein the receptacle comprises a capsule.

34. The unit dosage of claim 32, wherein the receptacle comprises a foil plastic laminate.

35. A unit dosage, comprising between about 0.5 mg and 15 mg of the composition of claim 19 within a receptacle.

36. An inhalation device, wherein the receptacle of claim 32 is within the inhalation device.

37. A composition comprising a plurality of inhalable particles, each comprising a drug and a pharmaceutically acceptable carrier, wherein the inhalable particles have an average particle size of less than 10 μm and a rugosity of at least 3, as determined by BET, centrifugal sedimentary particle size analysis, and pycnometry.

38. The composition of claim 37, wherein the rugosity ranges from 4 to 6.

39. The composition of claim 37, wherein the drug comprises a macromolecule.

40. The composition of claim 39, wherein the macromolecule is selected from proteins, polypeptides, oligopeptides, nucleic acids, and polysaccharides.

41. The composition of claim 39, wherein the macromolecule is selected from calcitonin, erythropoietin (EPO), factor IX, granulocyte colony stimulating factor, granulocyte macrophage colony stimulating factor, growth hormone, heparin, insulin, interferon alpha, interferon beta, interferon gamma, interleukin-2, leutenizing hormone releasing hormone (LHRH), somatostatin analog, vasopressin analog, follicle stimulating hormone (FSH), amylin, ciliary neurotrophic factor, growth hormone releasing factor (GRF), insulin-like growth factor, insulinotropin, interferon beta, interferon gamma, interleukin-3, interleukin-4, interleukin-6, macrophage colony stimulating factor (M-CSF), nerve growth factor, parathyroid hormone, thymosin alpha 1, factor IIb/IIIa inhibitor, alpha-1 antitrypsin, anti-RSV antibody, cystic fibrosis transmembrane regulator (CFTR) gene, deoxyribonuclease (DNase), bactericidal/permeability increasing protein (BPI), anti-CMV antibody, interleukin-1 receptor, and interleukin-1 receptor antagonist.

42. The composition of claim 37, wherein the pharmaceutically acceptable carrier comprises at least one member selected from carbohydrates, amino acids, buffers, and salts.

43. The composition of claim 42, wherein the pharmaceutically acceptable carrier comprises at least one member selected from monosaccharides, disaccharides, polysaccharides, and hydrophobic amino acids.

44. The composition of claim 42, wherein the pharmaceutically acceptable carrier comprises at least one member selected from mannitol, trehalose, sodium chloride, sodium citrate, leucine, lactose, raffinose, alanine, and glycine.

45. The composition of claim 37, wherein the particles have a moisture content below 10 wt %.

46. The composition of claim 37, wherein at least 90% by mass of the particles have a size between 0.1 μm and 7 μm.

47. The composition of claim 37, wherein at least 95% by mass of the particles have a size between 0.4 μm and 5 μm.

48. A composition comprising a plurality of inhalable particles, each comprising insulin and a pharmaceutically acceptable carrier, wherein the inhalable particles have an average particle size of less than 10 μm and a rugosity of greater than 3, as determined by BET, centrifugal sedimentary particle size analysis, and pycnometry.

49. The composition of claim 48, wherein the rugosity ranges from 4 to 6.

50. The composition of claim 48, wherein the pharmaceutically acceptable carrier comprises at least one member selected from carbohydrates, amino acids, buffers, and salts.

51. The composition of claim 50, wherein the pharmaceutically acceptable carrier comprises at least one member selected from monosaccharides, disaccharides, polysaccharides, and hydrophobic amino acids.

52. The composition of claim 50, wherein the pharmaceutically acceptable carrier comprises at least one member selected from mannitol, trehalose, sodium chloride, sodium citrate, leucine, lactose, raffinose, alanine, and glycine.

53. The composition of claim 48, wherein the particles have a moisture content below 10 wt %.

54. The composition of claim 48, wherein at least 90% by mass of the particles have a size between 0.1 μm and 7 μm.

55. The composition of claim 48, wherein at least 95% by mass of the particles have a size between 0.4 μm and 5 μm.

56. A composition comprising:

a plurality of inhalable particles having a rugosity of at least 2, as determined by BET, centrifugal sedimentary particle size analysis, and pycnometry, each of the plurality of inhalable particles comprising:

insulin; and a pH adjuster or buffer.

57. The composition of claim 56, wherein the rugosity is at least 3.

58. The composition of claim 56, wherein the rugosity ranges from 2 to 6.

59. The composition of claim 56, further comprising a pharmaceutically acceptable carrier.

60. The composition of claim 59, wherein the pharmaceutically acceptable carrier comprises one or more bulking agents.

61. The composition of claim 60, wherein the one or more bulking agents comprises at least one member selected from mannitol and glycine.

62. The composition of claim 61, wherein the pH adjuster or buffer comprises sodium citrate.

63. The composition of claim 56, wherein the particles have a moisture content of less than 10 wt %.

64. The composition of claim 56, wherein the particles have a moisture content of less than 5 wt %.

65. The composition of claim 56, wherein the composition has an average particle size of less than 10 μm.

66. A composition comprising:

a plurality of inhalable particles, each comprising insulin and a pharmaceutically acceptable carrier, wherein the inhalable particles are made by atomizing a liquid medium comprising the insulin, the pharmaceutically acceptable carrier, and ethanol to form droplets, and drying the droplets in a heated gas stream to produce the inhalable particles, and wherein the particles have a rugosity of at least 2, as determined by BET, centrifugal sedimentary particle size analysis, and pycnometry.

67. The composition of claim 66, wherein the rugosity is at least 3.

68. The composition of claim 66, wherein the rugosity ranges from 2 to 6.

69. The composition of claim 66, wherein the pharmaceutically acceptable carrier comprises a buffer.

70. The composition of claim 69, wherein the buffer comprises sodium citrate.

71. The composition of claim 66, wherein the particles have a moisture content of less than 10 wt %.

72. The composition of claim 66, wherein the particles have a moisture content of less than 5 wt %.

73. The composition of claim 66, wherein the composition has an average particle size of less than 10 μm.

74. The composition of claim 66, wherein the composition has an average particle size of less than 5 μm.

75. The composition of claim 66, wherein the pharmaceutically acceptable carrier comprises sodium citrate, and wherein the particles have a moisture content of less than 10 wt %.

76. A method of treating diabetes, comprising:

pulmonarily administering to the alveolar regions of the lungs of a subject a therapeutically effective amount of a composition comprising inhalable particles, each comprising insulin and a pharmaceutically acceptable carrier, wherein the inhalable particles have a rugosity of at least 2, as determined by air permeametry.

77. The method of claim 76, wherein the rugosity is at least 3.

78. The method of claim 76, wherein the rugosity ranges from 2 to 6.

79. The method of claim 76, wherein the rugosity ranges from 4 to 6.

80. The method of claim 76, wherein the pharmaceutically acceptable carrier comprises a buffer.

81. The method of claim 80, wherein the buffer comprises sodium citrate.

82. The method of claim 76, wherein the pharmaceutically acceptable carrier comprises a penetration enhancer.

83. The method of claim 76, wherein the particles have a moisture content of less than 10 wt %.

84. The method of claim 76, wherein the particles have a moisture content of less than 5 wt %.

85. The method of claim 76, wherein the composition has an average particle size of less than 10 μm.

86. The method of claim 76, wherein the composition has an average particle size of less than 5 μm.

87. The method of claim 76, wherein the rugosity is at least 3, and wherein the particles have a moisture content of less than 10 wt %.

88. The method of claim 76, wherein the rugosity is at least 3, wherein the composition further comprises sodium citrate, and wherein the particles have a moisture content of less than 10 wt %.

89. The method of claim 76, wherein the rugosity is at least 3, wherein the composition further comprises a penetration enhancer, and wherein the particles have a moisture content of less than 10 wt %.

90. A method of treating diabetes, comprising:

pulmonarily administering to the alveolar regions of the lungs of a subject a therapeutically effective amount of a composition comprising inhalable particles, each comprising insulin and a pharmaceutically acceptable carrier, wherein the inhalable particles have a rugosity of at least 2, as determined by BET, centrifugal sedimentary particle size, and pycnometry.

91. The method of claim 90, wherein the rugosity is at least 3.

92. The method of claim 90, wherein the rugosity ranges from 2 to 6.

93. The method of claim 90, wherein the rugosity ranges from 4 to 6.

94. The method of claim 90, wherein the pharmaceutically acceptable carrier comprises a buffer.

95. The method of claim 94, wherein the buffer comprises sodium citrate.

96. The method of claim 90, wherein the pharmaceutically acceptable carrier comprises a penetration enhancer.

97. The method of claim 90, wherein the particles have a moisture content of less than 10 wt %.

98. The method of claim 90, wherein the particles have a moisture content of less than 5 wt %.

99. The method of claim 90, wherein the composition has an average particle size of less than 10 μm.

100. The method of claim 90, wherein the composition has an average particle size of less than 5 μm.

101. The method of claim 90, wherein the rugosity is at least 3, and wherein the particles have a moisture content of less than 10 wt %.

102. The method of claim 90, wherein the rugosity is at least 3, wherein the composition further comprises sodium citrate, and wherein the particles have a moisture content of less than 10 wt %.

103. The method of claim 90, wherein the rugosity is at least 3, wherein the composition further comprises a penetration enhancer, and wherein the particles have a moisture content of less than 10 wt %.

104. A method of delivery of a composition to the lungs of a subject, the method comprising:

administering by inhalation a composition in aerosolized form, wherein the composition comprises inhalable particles, each comprising a drug and a pharmaceutically acceptable carrier, and wherein the inhalable particles have an average particle size of 10 μm and a rugosity of greater than 3, as determined by BET, centrifugal sedimentary particle size analysis, and pycnometry.

105. A method of delivery of a composition to the lungs of a subject, the method comprising:

administering by inhalation a composition in aerosolized form, wherein the composition comprises inhalable particles, each comprising insulin and a pharmaceutically acceptable carrier, and wherein the inhalable particles have a rugosity of at least 2, as determined by air permeametry, and wherein the composition has an average particle size of less than 10 μm.

106. A method of delivery of a composition to the lungs of a subject, the method comprising:

administering by inhalation a composition in aerosolized form, wherein the composition comprises inhalable particles, each comprising insulin and a pharmaceutically acceptable carrier, and wherein the inhalable particles have a rugosity of at least 2, as determined by BET, centrifugal sedimentary particle size analysis, and pycnometry, and wherein the composition has an average particle size of less than 10 μm.

* * * * *